United States Patent [19]

Merger et al.

[11] Patent Number: 4,634,558

[45] Date of Patent: * Jan. 6, 1987

[54] PREPARATION OF α-SUBSTITUTED ACRYLAMIDES

[75] Inventors: Franz Merger, Frankenthal; Wolfgang Schwarz, Pfinztal, both of Fed. Rep. of Germany

[73] Assignee: BASF Aktiengesellschaft, Fed. Rep. of Germany

[*] Notice: The portion of the term of this patent subsequent to Jul. 1, 2003 has been disclaimed.

[21] Appl. No.: 677,035

[22] Filed: Nov. 30, 1984

[30] Foreign Application Priority Data

Dec. 2, 1983 [DE] Fed. Rep. of Germany ....... 3343674

[51] Int. Cl.$^4$ ............................................ C07C 102/10
[52] U.S. Cl. .................................... 260/404; 564/124; 564/204
[58] Field of Search ................. 564/124, 204; 260/404

[56] References Cited

U.S. PATENT DOCUMENTS 4,365,092 12/1982 Harwell ............................... 564/135
4,408,079 10/1983 Merger et al. ...................... 568/463

FOREIGN PATENT DOCUMENTS 0058927 5/1984 European Pat. Off. ................ 45/75
3205946 9/1983 Fed. Rep. of Germany ...... 103/133
0128302 10/1977 Japan .

OTHER PUBLICATIONS

Recueil des Travaux Chimiques des Pays-Bas, vol. 96, 142 (1977).
Recueil des Travaux Chimiques des Pays-Bas, vol. 95, 123 (1976).
J. Am. Chem. Soc., 83, 193 (1961).
Houben-Weyl "Methoden der Organischen Chemie", vol. 10/4, pp. 55 et seq.

Primary Examiner—Charles F. Warren
Assistant Examiner—Carolyn S. Greason
Attorney, Agent, or Firm—Keil & Weinkauf

[57] ABSTRACT

α-Substituted acrylamides of the general formula I

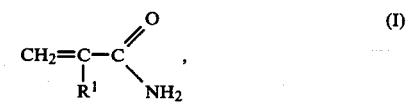

where $R^1$ is a straight-chain, branched or cyclic alkyl radical of not more than 15 carbon atoms which can be unsubstituted or further substituted, are prepared by a process in which the corresponding α-substituted acrolein oximes are heated at from 40° to 250° C. in the presence of a copper(II) carboxylate and of an unsubstituted or substituted acrylonitrile as cocatalyst.

4 Claims, No Drawings

PREPARATION OF α-SUBSTITUTED ACRYLAMIDES

The present invention relates to a novel process for the preparation of α-substituted acrylamides, starting from oximes of α-substituted acroleins.

α-Substituted acrylamides can be obtained by amidation of the particular esters with ammonia, or by hydration of the corresponding nitriles. However, only a limited number of the acrylates and acrylonitriles required for this purpose can be synthesized, and the synthesis is essentially restricted to the (meth)acrylyl compounds. Moreover, the amidation is technically complicated and does not take place particularly selectively, since side reactions, such as Michael addition reactions, can occur.

US-A U.S. Pat. No. 4,365,092 proposes the preparation of methacrylamide from methyl methacrylate, using aqueous ammonia solution. However, this method requires long reaction times and relatively large amounts of expensive anionic surfactants, which make isolation and purification of the amide more difficult.

Another route for the synthesis of methacrylamide starts from acetone cyanohydrin, methacrylamide sulfate being an intermediate. In this procedure, however, large amounts of salts are obtained and furthermore expensive purification steps have to be carried out.

For the preparation of acid amides, rearrangement reactions of aldoximes are also disclosed in the literature (J. Am. Chem. Soc. 83 (1961), 1983, Rec. Trav. Chim. Pays Bas 95 (1976), 123 and 96 (1977), 142). The aldehydes from which the aldoximes are derived generally belong to the class consisting of the saturated or aromatic aldehydes. The catalysts used are salts of nickel, zinc, palladium, cobalt or copper. Nickel(II) acetate and palladium(II) acetate have proven particularly effective, whereas, in the case of benzaldoxime, copper(II) acetate only results in undesirable reactions or gives poor yields.

In addition to the rearrangement of saturated aldoximes and benzaldoximes, JP-A-No. 128 302/1977 also describes the conversion of cinnamaldehyde oxime in the presence of copper acetylacetonate. However, we have found that the use of this complex in the preparation of α-alkyl-substituted acrylamides does not lead to satisfactory results.

Finally, DE-A-No. 3 205 946 proposes preparing methacrylamide from methacrolein oxime in the presence of a catalyst based on copper/chromium. In this catalyst, which advantageously should be used in the form of a supported catalyst, a defined molar ratio of copper to chromium is required.

However, the yield of methacrylamide in this process is only 72%. Moreover, we have found that, used alone, none of the copper salts stated therein, which constitute the copper component of the catalyst and are derived from formic acid, acetic acid or tartaric acid, gives the desired optimum results.

Because the syntheses, disclosed to date, of α-alkyl-substituted acrylamides are unsatisfactory and in general restricted to methacrylamide, it is an object of the present invention to prepare such compounds in a simpler and more economical manner.

We have found that this object is achieved and that, accordingly, α-substituted acrylamides of the general formula I

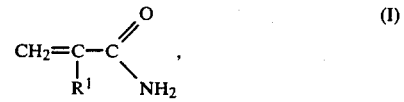

where $R^1$ is a straight-chain, branched or cyclic alkyl radical of not more than 15 carbon atoms which can be unsubstituted or further substituted, are advantageously obtained from an aldoxime of the general formula II

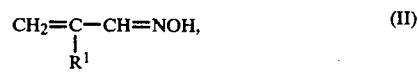

where $R^1$ has the above meanings, if the aldoxime is heated at from 40° to 250° C. in the presence of a carrier-free copper(II) carboxylate obtained from a monocarboxylic acid of 2 to 18 carbon atoms and in the presence of a nitrile of the general formula III

where $R^2$ is hydrogen or has the same meaning as $R^1$, as a cocatalyst.

The process according to the invention is carried out using an oxime of an acrolein which carries, in the -position, a straight-chain, branched or cyclic alkyl radical of not more than 15 carbon atoms. This alkyl radical can be substituted by further groups which are inert under the reaction conditions, for example lower alkoxy (also in the geminal positions), lower acyloxy, lower alkoxycarbonyl or lower mono- or dialkylamino groups.

Examples of α-alkyl-substituted acrolein oximes are α-methacrolein oxime, α-ethylacrolein oxime, α-butylacrolein oxime, α-(2-ethylhexyl)-acrolein oxime, α-nonylacrolein oxime, α-cyclohexylacrolein oxime, α-(4-methylcyclohexyl)-acrolein oxime, α-(3-carbethoxypropyl)-acrolein oxime and α-(4,4-dimethylaminobutyl)-acrolein oxime.

The α-substituted acroleins from which the aldoximes (II) are derived are readily obtainable by means of the process described in EP-A-No. 58 927, by reaction of an alkanal with formaldehyde and a secondary amine in the presence of an acid.

The aldoximes required for the novel process can be prepared from the α-substituted acroleins and hydroxylammonium salts by a conventional method, as described in, for example, Houben-Weyl, Methoden der organischen Chemie, volume 10/4, page 55 et seq., the acid liberated being neutralized with a base.

We have furthermore found that, in the preparation of the lower homologs of these aldoximes, in which the unsubstituted or substituted α-alkyl radical is of not more than 4 carbon atoms, the usual addition of a base can, surprisingly, be dispensed with. The formation and isolation of the aldoximes take place without neutralization of the acid and corresponding salt formation. The aqueous acid can be recycled, or used for neutralization purposes.

Advantageously, technical-grade aqueous hydroxylammonium salt solutions are used. Excess acid and its ammonium salts, as are present in such technical-grade solutions, do not present problems.

The rearrangement of the aldoximes to give the corresponding α-substituted acrylamides is carried out at from 40° to 250° C., preferably from 60° to 180° C., in particular from 80° to 150° C.

The reaction is preferably carried out under atmospheric pressure, but in some cases it is advantageous to employ superatmospheric pressure of not more than 20 bar.

A solvent need not be employed, but it is preferable to carry out the process in the presence of an inert solvent, such as toluene, xylene, mesitylene, chlorobenzene, nitrobenzene, tetralin, decalin, dioxane, dibutyl ether or n-butyl acetate.

According to the invention, the rearrangement reaction of the aldoximes is carried out in the presence of a carrier-free copper(II) carboxylate obtained from a monocarboxylic acid of 2 to 18 carbon atoms.

Suitable acids of this type are unsubstituted or substituted monocarboxylic acids containing a saturated or unsaturated straight-chain, branched or cyclic alkyl radical, aralkanoic acids, oxaalkanoic acids and aromatic carboxylic acids, e.g. acetic acid, propionic acid, 2-chloropropionic acid, isobutyric acid, 2-methylbutanoic acid, pentanoic acid, hexanoic acid, 2-ethylhexanoic acid, 3,5,5-trimethylhexanoic acid, decanoic acid, 9-decenoic acid, 9-dodecenoic acid, 9-octadecenoic acid, cyclohexanecarboxylic acid, phenylacetic acid, 1-phenylcyclopentane-1-carboxylic acid, methoxyacetic acid, benzonic acid, 3,5-dichlorobenzoic acid and naphthoic acid.

The copper salts required for the novel process can be prepared by a conventional method, for example by reacting the carboxylic acid with copper(II) carbonate, or by reacting a copper salt with an alkali metal or ammonium salt of the particular carboxylic acid.

The copper salts are employed in a carrier-free form, i.e. without the use of a carrier frequently employed in catalyst technology, and advantageously in the absence of chromium.

The amount of the copper(II) carboxylate used is from 0.1 to 5, preferably from 0.5 to 2, mol %, based on 1 mole of aldoxime.

The novel process is carried out using a nitrile of the general formula III

(III)

where $R^2$ is hydrogen or has the same meanings as those given above for $R^1$, as a cocatalyst.

It is used in an amount of from 1 to 200, preferably from 20 to 100, mol %, based on 1 mole of aldoxime.

Advantageously, the nitriles used are those which correspond to the oximes ($R^2$ identical to $R^1$), but it is also possible to use other acrylonitriles ($R^2$ different from $R^1$), for example the particularly effective and readily available unsubstituted acrylonitrile (in which $R^2$ is H).

A particular advantage of carrying out the novel process with acrylonitriles (formula III) as cocatalysts is that the amount of the copper(II) carboxylate employed can be restricted to the abovementioned low concentrations. The effect already known from the rearrangement of saturated or aromatic aldoximes (loc. cit), whereby the addition leads to an increase in the space-time yield, is also observed.

The novel process is usually carried out as follows: the aldoxime together with the copper(II) carboxylate and the nitrile, preferably in an inert solvent, is heated to the stated temperature. Either a batchwise or a continuous procedure can be employed. In order to be able to control the exothermic reaction more easily, it is advantageous if only some of the oxime is initially taken, and the remainder is added in the course of the reaction.

When the reaction is complete, the desired products are isolated by crystallization or extraction, and can be used directly for many purposes. They can be purified by recrystallization and, if desired, freed from traces of copper by ion exchange.

As a rule, from 95 to 100% of the amount of nitrile used as cocatalyst is recovered by simple distillation when the reaction is complete.

Further advantages of the novel process are the use of the acroleins, which are readily obtainable compared with the acrylates and which often serve as intermediates for the synthesis of the acrylates, and the fact that the aldoxime rearrangement takes place particularly selectively under the reaction conditions.

The amides obtained by the novel process are useful intermediates for the preparation of modifiable polymers, for example for dispersions and surface coatings.

The Examples which follow illustrate the invention.

EXAMPLE 1

Preparation of Methacrolein Oxime 370 g of a 98% pure methacrolein were added dropwise, in the course of one hour and at about 3° C., to 1,510 ml of a vigorously stirred solution containing 490.3 g of hydroxylammonium sulfate, 19.25 g of sulfuric acid and 30.83 g of ammonium sulfate. Thereafter, cooling was discontinued and the reaction mixture was stirred for a further 2 hours, its temperature increasing to 21° C. Analysis by gas chromatography showed that 97% of the methacrolein had been converted. The organic phase was separated off, the aqueous phase was extracted twice with ether, the combined organic phases were dried over magnesium sulfate and evaporated down in a rotary evaporator, and the residue was distilled in a thin-film evaporator (82° C./16 mbar). 387 g (yield 90%, based on methacrolein converted) of 99.6% pure methacrolein oxime were obtained.

EXAMPLE 2

30 g of methacrolein oxime, 239.1 g of methacrylonitrile and 12.35 g (1 mol %, based on oxime) of Cu(II) 2-ethylhexanoate in 1,800 g of o-xylene were heated at 110° C., while stirring. A further 270 g of methacrolein oxime were then added dropwise in the course of 15 minutes, and, when the addition was complete, stirring was continued for a further 10 minutes and the mixture was then cooled to room temperature. The precipitated methacrylamide was filtered off over a pressure filter.

The experiment was repeated three times more in the manner stated above, except that the mother liquor from the first batch was used, and no fresh methacrylonitrile was added. A total of 1,105 g (92.3%) of crude methacrylamide was obtained from all four batches. When the mother liquor was distilled, 201 g (85%) of the methacrylonitrile used were recovered.

EXAMPLE 3

418.8 g of 94% pure α-nonylacrolein oxime, 1,030 g of o-xylene, 94.6 g of 95% pure α-nonylacrylonitrile and 13.9 g (2 mol %, based on oxime) of Cu(II) 2-ethylhexanoate were heated at 130° C. A vigorous exothermic reaction began; after this reaction had abated, stirring was continued for a further 1.5 hours at 110° C. Analysis by gas chromatography showed that 98.8% of the oxime used had been converted. 1.2 liters of petroleum ether were added to the reaction mixture, the latter was then cooled to −20° C., and the crude amide precipitated was filtered off under suction. Recrystallization from cyclohexane gave 332 g (84%) of α-nonylacrylamide as colorless crystals of melting point 80°–81° C.

EXAMPLE 4

In a 100 liter stirred kettle, 35.5 kg of xylene (isomer mixture), 1.06 kg of ethylacrylonitrile and 0.215 kg of Cu(II) acetate were refluxed at about 135° C., and 7.8 kg of 83% pure ethylacrolein oxime were then added in the course of 25 minutes. After 10 minutes, the stirred reaction mixture was cooled, first with water and then with brine, until its temperature had reached −6° C. The ethylacrylamide was filtered off over a suction filter and washed with petroleum ether. The crude yield was 5.956 kg (92%).

We claim:

1. A process for the preparation of an α-substituted acrylamide of the formula I

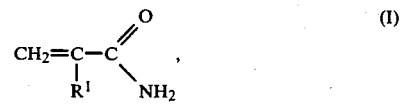

where $R^1$ is a straight-chain, branched or cyclic alkyl radical of not more than 15 carbon atoms which can be unsubstituted or further substituted, from an aldoxime of the formula II

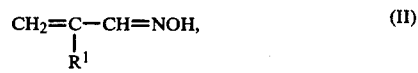

where $R^1$ has the above meanings, wherein the aldoxime is heated at from 40° to 250° C. in the presence of a carrier-free copper(II) carboxylate obtained from a monocarboxylic acid of 2 to 18 carbon atoms and in the presence of a nitrile of the formula III

where $R^2$ is hydrogen or has the same meaning as $R^1$, as a cocatalyst.

2. The process of claim 1, wherein the reaction is carried out at from 60° to 180° C.

3. The process of claim 1, wherein the reaction is carried out under atmospheric pressure.

4. The process of claim 1, wherein the reaction is carried out in the presence of an inert solvent.

* * * * *